United States Patent [19]

Swendson et al.

[11] Patent Number: 5,803,770

[45] Date of Patent: Sep. 8, 1998

[54] CONNECTOR FOR ELECTRICAL CABLE AND METHOD OF MAKING

[75] Inventors: David L. Swendson, Garden Grove; David J. Evans, Irvine, both of Calif.

[73] Assignee: Baxter International Inc., Deerfield, Ill.

[21] Appl. No.: 468,088

[22] Filed: Jun. 6, 1995

Related U.S. Application Data

[63] Continuation-in-part of Ser. No. 200,619, Feb. 23, 1994, Pat. No. 5,564,951.

[51] Int. Cl.$^6$ ........................................... H01R 23/02
[52] U.S. Cl. ........................... 439/676; 29/843; 439/606; 439/930; 439/948
[58] Field of Search ...................... 439/676, 344, 439/493, 76.1, 604, 606, 930, 948; 29/883, 874, 843

[56] References Cited

U.S. PATENT DOCUMENTS

| | | | |
|---|---|---|---|
| 3,065,445 | 11/1962 | Crimmons | 439/496 |
| 3,149,897 | 9/1964 | Martineck | 439/494 |
| 3,258,831 | 7/1966 | Angele et al. | 29/884 |
| 3,696,319 | 10/1972 | Olsson | 439/496 |
| 4,497,526 | 2/1985 | Myers | 439/676 |
| 4,703,989 | 11/1987 | Price | 439/283 |
| 4,731,031 | 3/1988 | Lemke | 439/76.1 |
| 4,786,259 | 11/1988 | Paul | 439/344 |
| 4,806,117 | 2/1989 | Johnston | 439/344 |
| 4,825,876 | 5/1989 | Beard | 128/675 |
| 4,878,848 | 11/1989 | Ingalsbe | 439/676 |
| 5,015,197 | 5/1991 | Redmond et al. | 439/329 |
| 5,048,531 | 9/1991 | Spotts et al. | 128/675 |
| 5,074,039 | 12/1991 | Hillbish et al. | 29/883 |
| 5,074,801 | 12/1991 | Siemon | 439/188 |
| 5,091,826 | 2/1992 | Arnett et al. | 439/676 |
| 5,135,002 | 8/1992 | Kirchner et al. | 128/672 |
| 5,147,215 | 9/1992 | Pritulsky | 439/344 |
| 5,178,563 | 1/1993 | Reed | 439/676 |
| 5,217,388 | 6/1993 | Brown | 439/455 |
| 5,304,074 | 4/1994 | Andre et al. | 439/676 |

FOREIGN PATENT DOCUMENTS

| | | |
|---|---|---|
| 0583486 | 2/1994 | European Pat. Off. |
| 2223126 | 11/1972 | Germany |
| 2704806 | 8/1978 | Germany |
| 3630380 | 3/1988 | Germany |
| 2231210 | 11/1990 | United Kingdom |

*Primary Examiner*—Neil Abrams
*Attorney, Agent, or Firm*—Guy L. Cumberbatch; Bruce M. Canter

[57] ABSTRACT

A female electrical connector (164') is carried on an electrical cable (24') including plural electrical conductors (28'). The female connector includes an insulative housing (34a', 34b') defining a blind cavity (36') therewithin and an axial opening outwardly from the cavity. The housing carries a printed circuit board (166) carrying plural wire-like contacts (40') which individually connect with the conductors of the electrical cable. The wire-like contacts extend into the cavity of the connector for deflecting in spring-like contact with electrical contacts (60) carried by a male connector (20) when the latter is inserted into the cavity of the female connector. A comb feature (50') of the female connector is formed by a strong end wall (138') of the blind cavity and in a respective one of plural slots (48') of the comb feature movably receives a free end portion (46') of each one of the plural wire-like contacts. The wire-like contacts are free to move in the cavity in spaced apart parallel relationship between a first position against or adjacent to a shelf surface (52') of the comb feature and the second position spaced from the shelf feature as the matching male connector is mated with the female connector. The end wall (138') of the female connector carries a stop member (190) preventing the male connector from damaging either the wire-like contacts or comb feature of the female connector when the male connector is inserted into the female connector too forcefully. Structural features (76', 192) of the female connector allow the insulative housing to be injection molded using dies which open only in the axial direction.

14 Claims, 8 Drawing Sheets

CONNECTOR FOR ELECTRICAL CABLE AND METHOD OF MAKING

CROSS REFERENCE TO RELATED APPLICATION

The present application is a Continuation-in-Part of U.S. application Ser. No. 08/200,619, filed 23 Feb. 1994, now U.S. Pat. No. 5,564,951, which is assigned to the same assignee as is the present application, and the disclosure of which is hereby incorporated herein by reference as though it were fully set out.

BACKGROUND OF THE INVENTION

1. Field of the Invention

The present invention is in the field of connectors for electrically interconnecting electrical conductors of electrical cables. More particularly, the present invention is in the field of connectors for multi-conductor electrical cables, in which the connector provides for individual connection of each conductor of the multi-conductor electrical cable to a corresponding electrical conductor of another multi-conductor electrical cable, or to other structure.

2. Related Technology

Current technology includes a wide variety of multi-conductor electrical cables, and a similarly wide variety of connectors for such cables. These connectors generally provide for individual connection of the electrical conductors of a cable either to the corresponding conductors of another cable or to other electrical structure. For example, in the home, the common two-conductor or three-conductor electrical extension cord for house-current is well-known. This extension cord includes a male connector plug at one end and a female connector receptacle at the other end.

Another common example of a multi-conductor electrical cable connector is the modular telephone connector presently in wide use. This connector provides for electrically connecting up to five conductors of a telephone cable either to five corresponding conductors of another length of telephone cable, or to corresponding conductors of another structure, such as a telephone. In the case of both the house-current extension cord and the modular telephone connector, the actual electrical interconnection between cables or other structures is effected by mutual contact of pre-formed or stamped metallic contacts carried by a pair of connectors. Frequently, these metallic contacts are formed of a springy and shape-retaining material, such as phosphor-bronze. When the connectors of a pair are engaged with one another, the contacts distort slightly into electrical contact as the male and female components of the connector pair, such as a plug and receptacle, for example, are engaged with one another.

In the process of manufacturing many connectors for multi-conductor electrical cables, the pre-formed contacts are attached by soldering or crimping to individual end portions of each conductor from which the electrical insulation has first been stripped. Subsequently, these contacts are placed into receiving portions of a mold cavity which also has provision for sealingly closing about the adjacent length of cable. This mold cavity defines a void space which is configured to the selected shape of the finished connector. The mold cavity void space may be filled with a thermoplastic insulative material, such as polyvinylchloride, for example, or with a thermoset insulative material, such as natural or synthetic rubber. Injection molding or transfer molding, for example, may be used to fill the mold cavity void space with insulative material. After the insulative material cools or cures, the cable and connector with electrical contacts completely enclosed (in the case of a female connector) or partially embedded in insulative material and outwardly projecting therefrom (in the case of a male connector), is removed from the mold cavity.

As can be appreciated from the above, the conventional cable connectors require the fabrication of plural component parts, and the performance of plural manufacturing steps in order to complete the connector. All of these component parts and plural manufacturing steps add to the overall cost of a conventional cable connector. Also, the multiplicity of parts and manufacturing steps for a conventional cable connector increases the opportunity for variability in the manufacturing process, and for quality control problems and high scrap rates.

A conventional multi-conductor electrical cable and connector is known in accord with U.S. Pat. No. 4,703,989 (hereinafter, the '989 patent), issued 3 Nov. 1987, to J. R. Price, et al. The electrical connector and cable of the '989 patent are employed to connect a disposable blood pressure monitoring assembly to a durable, or reusable, cable and connector. This latter durable cable and connector are connected to a blood pressure monitoring apparatus. The connector and cable of the disposable blood pressure sensor assembly employs plural individual electrically conductive blade members of the so called, "insulation-displacement" type to penetrate the insulation of the cable into electrical contact with the corresponding electrical conductors. These insulation-displacement blades then provide for electrical connection of the respective conductors of the cable to corresponding contacts of the connector carried on the durable cable extending to the monitor.

With a cable connector according to the '989 patent, all of the deficiencies of conventional cable connectors apply. Further, because the cable, its connector, and a molded housing for the blood pressure sensing unit may be manufactured together in a semi-continuous process, defects in the connectors which render them unusable also require the connected length of cable and molded sensor housing also to be scrapped.

Another conventional connector is known in accord with U.S. Pat. No. 5,147,215 (hereinafter, the '215 patent), issued 15 Sep. 1992 to James Pritulsky, and assigned to AMP Incorporated. The connector disclosed by the '215 patent is believed to disclose the use of a cavity with a bottom wall having plural longitudinal ribs each provided with an insulation piercing contact. The conductors of a multi-conductor cable are arrayed in the cavity and in the grooves between adjacent ribs of the bottom wall thereof. The contacts have a surface disposed away from the conductors and to which a force may be applied to force the insulation-piercing portion of the contacts through the insulation of the cable conductors into electrical contact with the electrical conductors therein.

Viewing FIGS. 1–11, a conventional prior art disposable blood pressure sensor assembly 10 includes a sensor module 12, with fluid connection ports at 14. A strain-gauge type of pressure sensor (not shown) is housed within a central case portion 16, and communicates with the ports 14. From the case portion 16 and the strain gauge sensor therein extends a multi-conductor cable 18. The cable 18 extends to, carries, and forms a part of a connector 20, which is to be further described.

Figures 1, 2, 4:
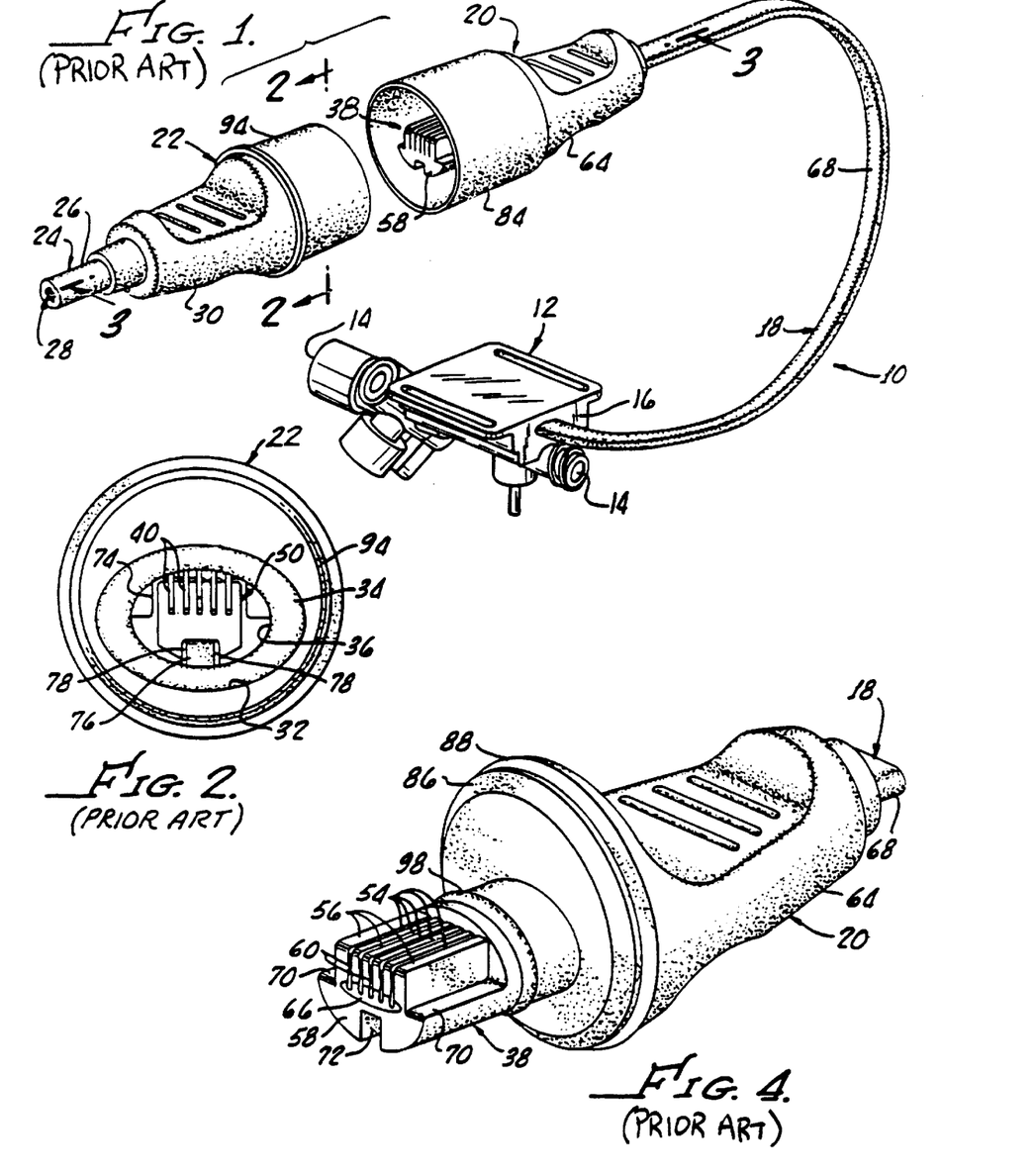
FIG. 1 provides a perspective view of a disposable prior art pressure sensor module with attached cable and cable connector, the latter in confronting relation with a prior art durable cable with cable connector, preparatory to interconnection of these connectors.
FIG. 2 is an enlarged end view of the durable prior art cable connector taken at the line 2—2 of FIG. 1 and looking in the direction of the arrows.
FIGS. 4 and 5 are respective fragmentary upper quarter and lower quarter perspective views of the disposable prior art cable connector seen in FIGS. 1–3, and having a portion thereof removed for clarity of illustration.

Juxtaposed in confronting relationship with the connector 20, is a matching connector 22 carried on a length of cable 24. The cable 24 may be similar to the cable 22 in having the same number of electrical conductors therein, or may be identical with the cable 22. The cable 24 and connector 22 lead to and are electrically attached to a blood pressure monitoring apparatus (not shown). Cable 24 includes an insulating jacket 26, and plural electrical conductors 28. As will be explained, the connectors 20, 22 provide for individual electrical connection of each of the plural electrical conductors 28 to corresponding conductors (identified below) of the cable 18.

Figure 3:
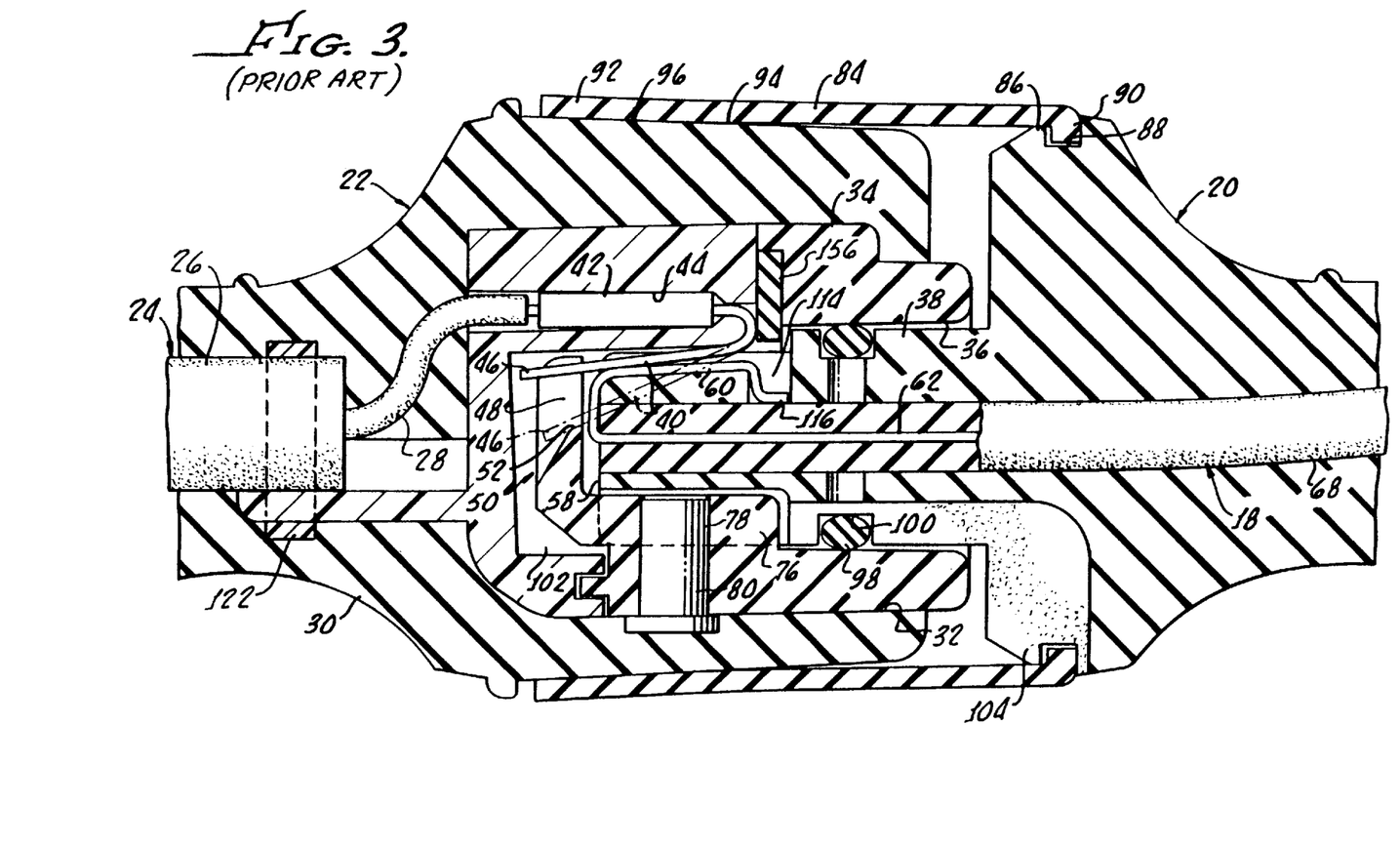
FIG. 3 is an enlarged fragmentary longitudinal cross sectional view taken generally at the plane indicated by the line 2—2 of FIG. 1, and through both of the connectors seen in this Figure as they appear when interconnected.
Figure 5:
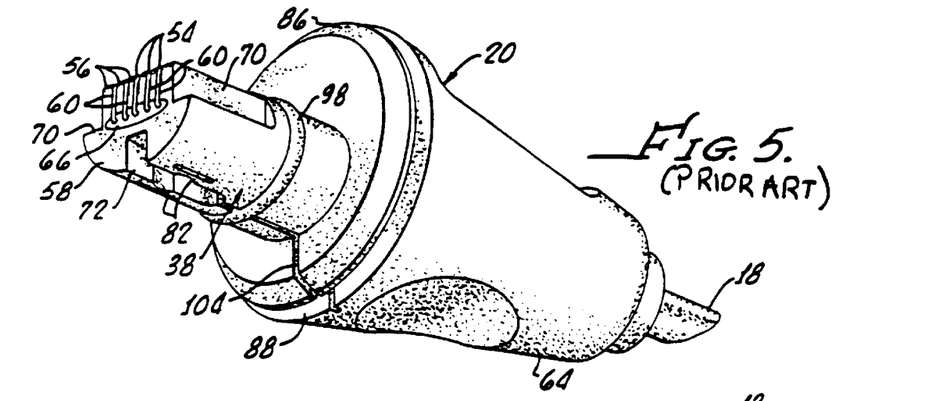
Figures 6, 7:
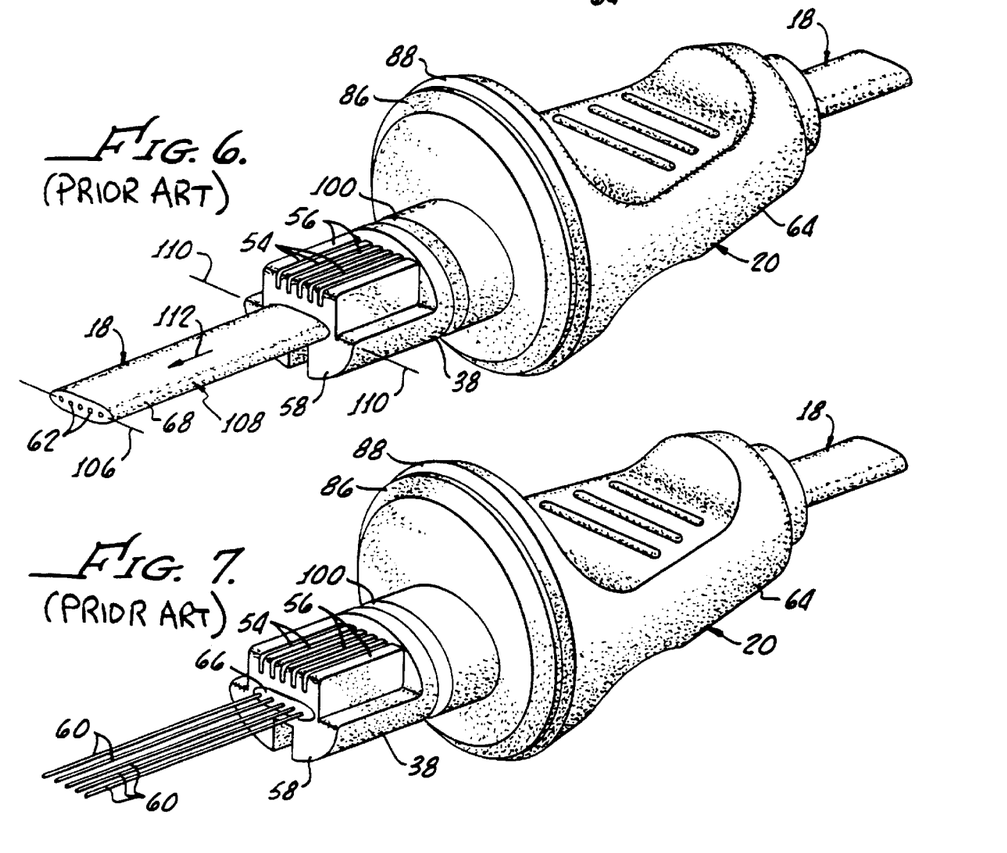
FIGS. 6 and 7 provide fragmentary perspective views of work pieces at successive steps in the processes of making a disposable prior art connector which is used in combination with a connector according to the present invention.

Viewing FIGS. 1, 2, and 3, it is seen that the connectors 20, 22 may be engaged or connected with one another. The connector 22 includes a body 30 of insulative material molded onto the cable 24, and defining a cavity 32 into which a preformed shape-retaining insulative member 34 is received. This pre-formed insulative member 34 defines a cavity 36 which is oval in end view, and into which a shape-matching and axially projecting portion 38 of the connector 20 is received. Within the cavity 36, the connector 22 carries a laterally arrayed plurality of spaced apart resilient wire-like contacts 40. These contacts 40 are each individually carried by a respective connector sleeve 42 which fits within a respective one of a regularly spaced laterally arrayed plurality of bores 44 (only one bore being seen in FIG. 3) defined by the member 34 above the cavity 36 as seen in FIG. 3.

As FIG. 3 shows, a respective one of the plural conductors 28 of the cable 24 is received by each corresponding one of the sleeves 42. Also, the contacts 40 are each individually movable at a free end portion 46 thereof in a respective slot 48 defined by a comb portion 50 of the member 34. As FIG. 3 shows in dashed lines, when the connectors 20, 22 are not connected, the free end portions 46 rest upon a respective shelf feature 52 of the comb 50. When the connectors 20, 22 are connected, the contacts 60 engage the contacts 40, and moves them to the solid line position seen in FIG. 3. The contacts 40 are positioned and movably spaced apart by the cooperation of the comb member 50 and the regular spacing of the plural sleeves 42 in bores 44.

Viewing FIG. 4, it is seen that the projecting portion 38 of connector 20 includes plural elongate slots 54 defined between separating wall portions 56 of the portion 38. These slots 54 open on an end surface 58 of the connector portion 38. The slots 54 are regularly spaced laterally to match the spacing and positioning of the contacts 40 within cavity 36. Returning to consideration of FIG. 3, it is seen that in the solid-line position of the contacts 40, each is received into a corresponding one of the slots 54 and in engagement with a conductor contact portion 60 of plural electrical conductors 62 in and extending outwardly of the cable 18.

FIG. 4 also shows that the connector 20 includes a body 64 of insulative material formed on the cable 18. The body 64 defines the projecting portion 38, and also in part defines the end surface 58. However, a central portion 66 of the end surface 58 is defined by the end of an insulative jacket 68 of the cable 18. As will be further explained, the conductors 62 are stripped of insulation beyond the surface 66 of jacket 68, and are wrapped over this surface 66 and over surface 58 into corresponding ones of the slots 54 between wall portions 58 to define the conductor contact portions 60.

It is well to note from FIGS. 1–5, that the connectors 20 and 22 define several cooperative features for purposes of relative positioning (or polarizing), for detenting, for shielding, and for environmental protection of the connectors 20, 22 and contacts 40, 60. For purposes of polarizing the connectors 20, 22, the portion 38 defines a pair of re-entrant grooves 70 and a slot 72. The cavity 36 of member 34 is formed with a pair of matching shoulders 74 and a key 76. An end 78 of a pin 80 in the member 34 projects into the cavity 36, interrupts key 76, and forms a cylindrical enlargement on this key. At the slot 72, viewing FIG. 5, the slot 72 is formed with a pair of semi-cylindrical enlargements 82 which receive the end 78 of pin 80 to detent the connectors 20, 22 in engagement with one another when they are engaged to their position seen in FIG. 3.

Shielding of the projecting portion 38 of connector 20, and of the contact portions 60 thereon is provided by a resilient shape-retaining sleeve member 84 which is carried on a matching cylindrical shoulder 86 of the connector 20. At the shoulder 86 the body 64 defines a circumferential groove 88, and the sleeve member 84 defines a collar portion 90 extending radially into the groove 88. A free end portion 92 of the sleeve member 84 defines an inner diameter which is slightly smaller than the outer diameter of a slightly tapered, but generally cylindrical portion 94 of the body 32. Consequently, when the connectors 20, 22 are connected as shown in FIG. 3, the free end portion 92 stretches slightly in diameter over the cylindrical portion 94 to form a moisture-resistant interference fit, indicated with the arrow 96.

In order to provide further environmental protection for the contacts 40, 60, the portion 38 carries an O-ring sealing member 98 in a circumferential groove 100. This O-ring sealing member cooperates with the portion 38 and with member 34 to form a chamber 102 in the cavity 36. The chamber 102 is closed by the sealing member 98 with the exception of a narrow vent slot 104 seen in FIGS. 3 and 5. This vent slot 104 is necessary to allow the escape of air from the chamber 102 during connection of the connectors 20, 22. If pressurized air were trapped in the chamber 102, it might cause uncoupling of the connectors 20, 22. However, while the narrow vent slot 104 is sufficient to allow the escape of air from chamber 102, it does not adversely effect environmental protection of the contacts 40, 60 because its narrow size causes the surface tension of liquids to prevent entry of these liquids into the cavity 102. Also, because the slot 104 forms the only entrance to the chamber 102, air trapped in this chamber precludes the entry of liquid into the chamber 102, even if the coupled connectors 20, 22 are immersed in liquid, for example.

With attention first to FIG. 4, it is seen that the insulative connector body 64 is formed on a length of the cable 18. Preferably, a number of the insulative connector bodies 64 are formed at selectively spaced apart locations on a long length of the cable 18. This formation of the plural connector bodies 64 on the length of cable can be performed in a semi-continuous manufacturing process. The insulative connector bodies 64 are preferably spaced regularly apart on a length of cable 18. The cable length is cut into sections at respective cut lines 106, each spaced from the end surface 58 of the corresponding body 64 so that each cable section has one insulative connector body 64 therein. This location of the cut line 106 results in a length 108 of cable 18 with jacket 68 and conductors 62 extending beyond the surface 58 of portion 38.

At a cut line 110 substantially coextensive with the surface 58, the jacket 68, but not conductors 62, is cut. The cut jacket portion is axially stripped from the conductors 62 (as is indicated by arrow 112), so that projecting conductor contact portions 60 result, viewing FIG. 7. The exposed cut end surface of the jacket 68 forms the central portion 66 of surface 58. At this point a further manufacturing step which is described in connection with FIG. 8 may be performed, or more preferably, one or more intermediate and preparator steps may be performed.

These intermediate and preparatory steps mentioned above involve the provision on the conductor contact portions 60 of a corrosion-resistant coating. Preferably, the conductors 62 are single-strand copper wires. In this case, the conductor contact portions 60 can be plated first with a material, such as nickel, to provide a hard and rigid base for bonding of a top coat of corrosion-resistant material. The corrosion-resistant material is preferably gold or silver. On the other hand, the conductors 62 may be of multi-strand construction, such as a bunch-stranded or a concentric-stranded conductor. For example, the conductors 62 may be of 7-strand (6 around 1) or 19-strand (11 around 7 around 1) concentric-stranded copper wire. In these cases, the multi-strand conductor can be top-coat plated as a group to form the conductor contact portion 60. This top coat plating locks the individual strands of each conductor 62 together with the other strands of this conductor in the stripped and projecting conductor contact portion 60 so that this conductor contact portion 60 acts as a single piece or like a single-strand wire for further forming. After the top coat plating, a corrosion-resistant coating of gold or silver, for example, may also be applied to the contact portions 60.

Figure 8:
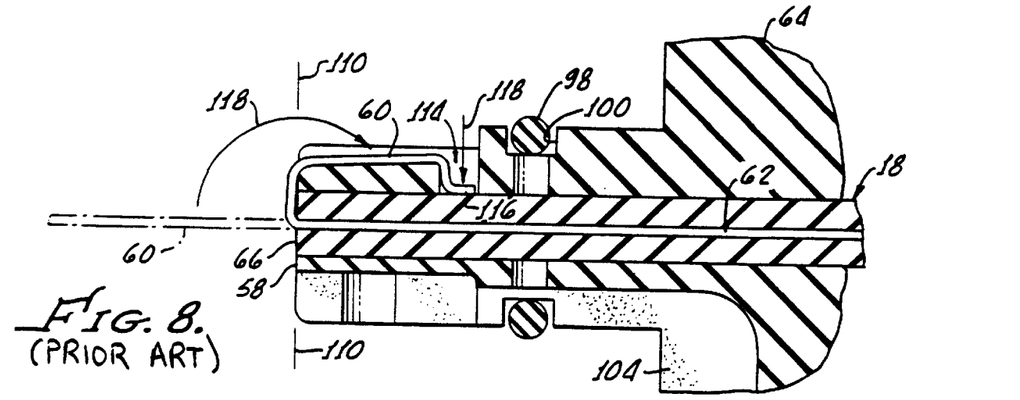
FIG. 8 is a fragmentary cross sectional view depicting a step in the process of making a disposable prior art connector for use in combination with a durable connector according to the present invention, which step is subsequent to the steps and resulting work pieces seen in FIGS. 6 and 7.

FIG. 8 shows that the conductor contact portions 60, whether they are single-strand wires or multi-strand wires top-coat plated into a unitary group, are each then bent across the end surfaces 58 and 66, and are further bent back on themselves into a corresponding one of the slots 54, still viewing also FIG. 4. The slots 54 are sized so that the conductor contact portions 60 lead into these slots. Remote from the end surface 58, each slot 54 includes a narrower portion 114 into which an end part 116 of the conductor contact portion 60 is forced in order to secure the remainder of the contact portion 60 in slot 54. The remainder of the conductor contact portion 60 is seen to extend generally axially. Folding of the portions 60 into the slots 54 and recesses 114 is shown by arrows 118 in FIG. 8.

Figure 9:
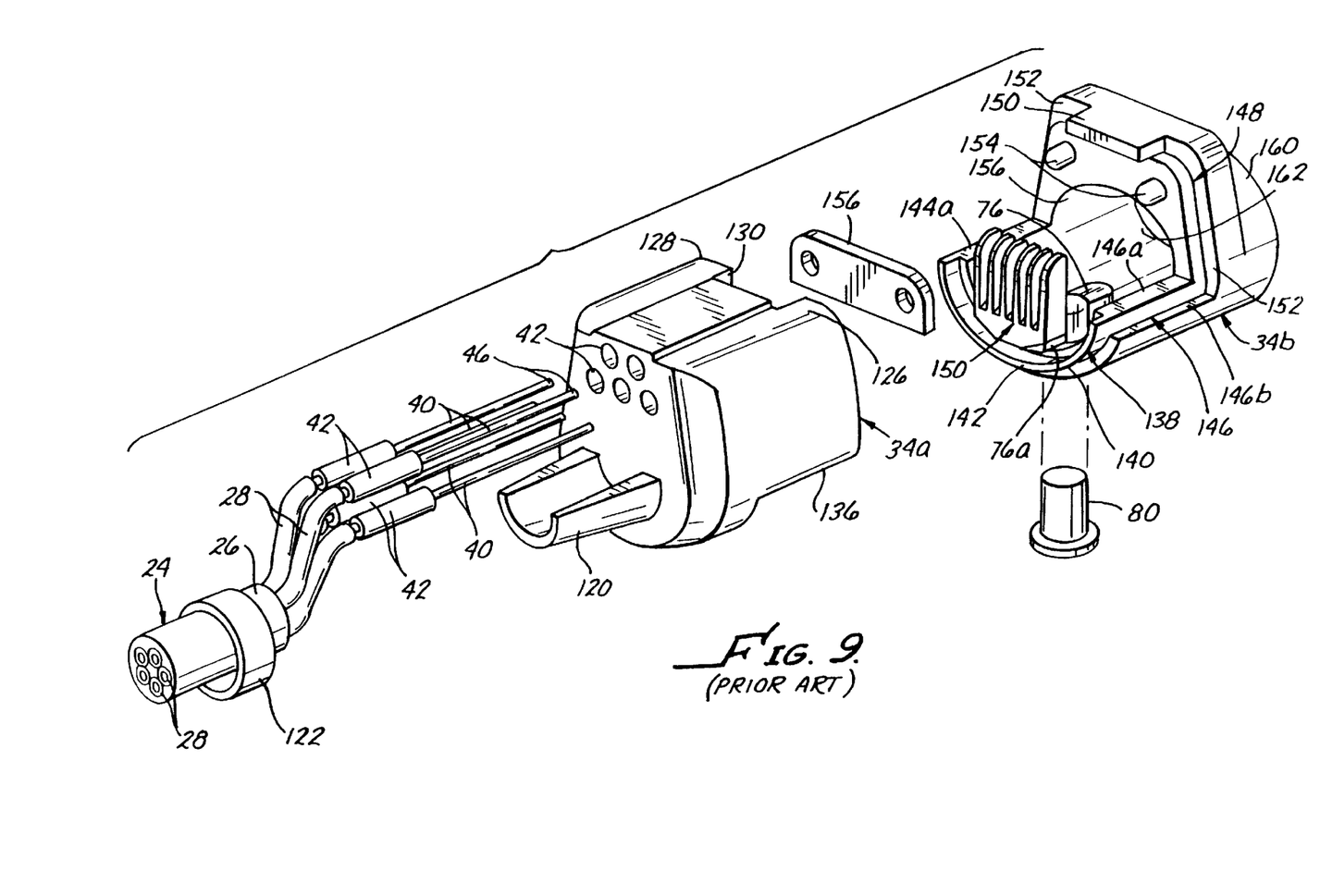
FIG. 9 provides a very greatly enlarged and exploded perspective view of parts of a durable prior art connector.
Figure 10:
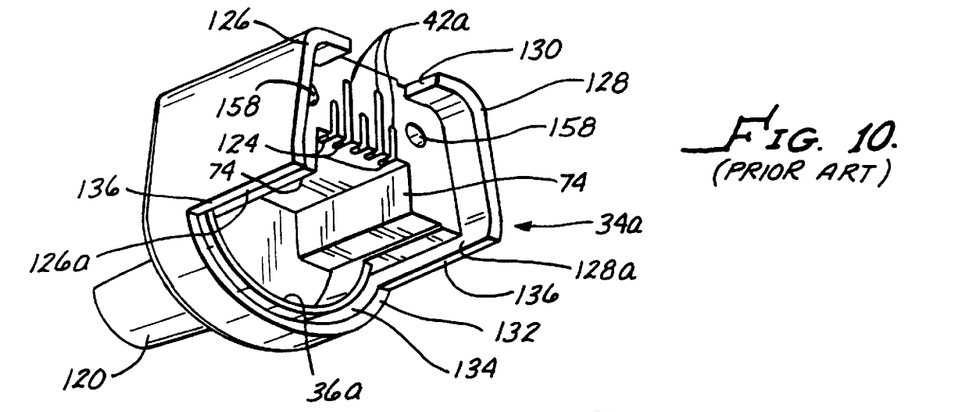
FIG. 10 is an enlarged perspective elevation view of a part of the durable prior art connector seen in FIG. 9.

FIG. 9 in conjunction with FIGS. 1, 2, 10, and 11 depict the connector 22 in greater detail. FIG. 9 shows an exploded perspective view of the connector 22 at an intermediate stage of manufacture and prior to the molding of the body portion 30 around the cable 24 and insulative member 34. As FIG. 9 shows more particularly, the insulative member 34 is formed of two cooperative parts, referenced with the numbers 34*a* and 34*b* on FIG. 9. It is seen in FIG. 3 that the bores 44, which are formed in part 34*a*, are stepped to receive at the ends of these bores adjacent to cable 24 the combined connectors 28, sleeves 42 and wire-like contacts 40 (the contacts 40 at this time being in a straight conditions as seen in FIG. 9). The steps on the bores 44 prevent the sleeves 42 from passing through the bores 42 so that the contacts 40 project from a smaller diameter portion 42*a* of the bores (as is best seen in FIG. 10). Viewing FIG. 9, it is seen that the part 34*a* includes an arcuate tang 120 to which the cable 24 may be secured by use of a crimping sleeve 122, seen in FIGS. 3 and 9. With the part 34*a* and cable 24 so prepared with contacts 40, the projecting free end portions 46 of the contacts are bent downwardly and rearwardly into the cavity 36 (the portion 36*a* of which is formed in the part 34*a*, as is best seen in FIG. 10).

Viewing FIG. 10 it is seen that the part 34*a* defines individual guide grooves 124 for receiving the individual contacts 40 so as to guide the free end portions 46 thereof downwardly from the bores 44 along the grooves 124 and rearwardly into the cavity portion 36*a* in a parallel spaced apart relationship. Still viewing FIG. 10, it is seen that the part 34*a* at an upper extent thereof includes a pair of wall portions 126, 128 that extend toward the viewer of this Figure and cooperatively define a notch 130 therebetween. Below the wall portions 126, 128, and spaced behind these features, the part 34*a* defines an arcuate wall 132 defining a forwardly opening arcuate groove 134. The wall portions 126, 128 are spaced forwardly of the arcuate wall by a longitudinally extending edge 136 on each side, so that the part 34*a* defines a Z-shaped surface for interface with the part 34*b*, as will be seen.

Figure 11:
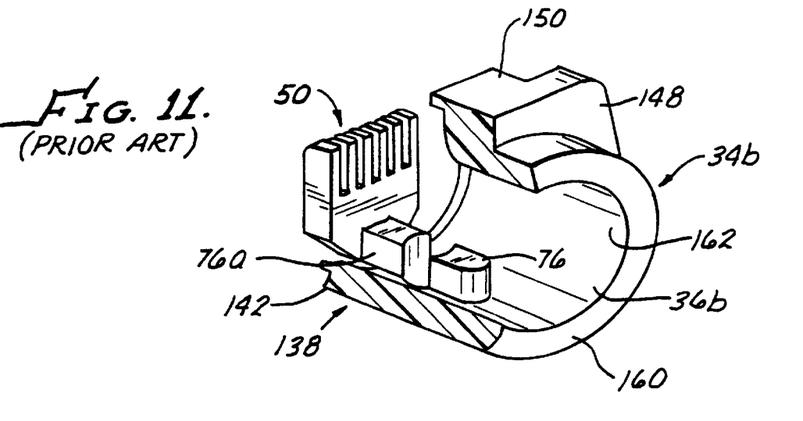
FIG. 11 is a fragmentary perspective view of another part of the durable prior art connector seen in FIG. 9, with a portion of the connector broken away and removed to better show salient features of the connector.

Viewing FIGS. 9 and 11, it is seen that the part 34*b* also forms a Z-shaped interface for cooperative engagement with the part 34*a*. That is, this Z-shaped interface of the part 34*b* is formed in part by a lower arcuate wall 138. This arcuate wall 138 has an arcuate end surface 140 at which is defined an arcuate tongue 142. The arcuate tongue 142 is received into the arcuate groove 134 of part 34*a*. The arcuate wall portion 138 has longitudinal edge surfaces 144, 146, which each include a respective up-raised inner portion 144*a* and 146*a*, and respective ledge features (144*b* and 146*b*, respectively, only the near-side ledge feature 146*b* being clearly visible in FIG. 9) outwardly of these up-raised inner portions. The up-raised inner portions 144*a* and 146*a* engage within depending lower portions 126*a* and 128*a* of walls 126 and 128 (seen in FIG. 10), while the ledge portions 146*b* and 146*b* engage the lower edge surfaces of these wall portions 126 and 128 of the part 34*a*.

In order to cooperate with the wall portions 126, and 128 of the part 34*a*, the part 34*b* includes a wall portion generally referred to with the numeral 148. this wall portion defines a rearwardly extending key 150 which is receivable into the notch 130 defined between the pair of wall portions 126 and 128. On each side of this key 150, the wall portion 148 includes a ledge surface 152 extending from the key feature 148 to the respective ledge surface 144*b*, 146*b* of each edge surface 144, 146. The wall portions 126, 128 of the part 34*a* are engageable at their ends with the wall portion 148 with the inner surfaces of these wall portions 126, 128 engaging onto the respective ledge surfaces 152. The part 34*b* defines its respective portion 36*b* of the cavity 36.

On the rear side of the wall portion 148, viewing FIG. 9, this wall portion carries a pair of rearwardly extending pegs 154. Carried on these pegs 154 is a pressure pad member 156 formed of elastomeric material. FIG. 10 shows that the member 34*a* includes a pair of holes 158 for receiving the ends of the pegs 154 so that the pressure pad member 156 is trapped between the portions 34*a* and 34*b* when these portions are united. As so trapped between the portions 34*a* and 34*b*, the pressure pad member 156 applies a resilient force to the bend of the contacts 40 between the bores 44 and the cavity 36 as these contacts extend along the guide grooves 124. This resilient pressure force applied from outside of the bend of the contacts 40 as they extend toward the free end portions 46 thereof, assists in avoiding stress concentrations in the bend of these wire-like contacts, and avoids stress cracking and early failure of the contacts 40 as these contacts flex with repeated connection and disconnection of the connectors 20 and 22.

Viewing FIG. 11, it is seen that from the forward side of the wall portion 148 extends an oval protrusion 160 which defines an oval opening 162 to the cavity 36*b* defined within the part 34*b*, and to the cavity 36 defined within the parts 34*a* and 34*b* when united. FIGS. 9 and 11 viewed in concert with one another show that within this cavity portion 36*b* the portion 34*b* includes a rear portion 76*a* of the key 76. The rear part 76*a* of the key 76 extends rearwardly beyond the arcuate end surface 140 into the cavity 36 to there support the comb member 50. When the member 34*b* is united with the portion 34*a*, which has been prepared as outlined above, the comb 50 first enters the cavity portion 36a within the portion 34a and receives the free end portions 46 of the contacts 40 individually into respective ones of the slots 48. Consequently, the comb member separates and confines the free end portions 46 to move in a vertical direction as the connector 20 is engaged and disengaged with the connector 22, recalling FIG. 3. The spacing of the slots 48 in the comb 50 matches precisely the spacing of the slots 54 in the connector 20, and the end surface 58 of portion 38 of connector 20 closely approaches and aligns with the comb 50 because of the engagement of the key 76 into the slot 72 of the connector 20. Consequently, when the connectors 20 and 22 are connected together, the contact free end portions 46 of connector 22 precisely align with and contact the connector portions 60 of the connector 20. After the parts 34a and 34b are combined as explained above, and the pin 80 is inserted, the body portion 30 is molded around the connector part 34, recalling FIGS. 1 and 3.

A disadvantage of the present connector 22 resides in the possibility for the conductors 28 of cable 24 not being permanently connected within the sleeves 42. That is, one or more of these conductors 28 may become loosened or disconnected from its corresponding sleeve 42 in response to handling and manipulation of the cable 24. Also, the connector 22 includes a comparatively large number of parts, which results in a comparatively high manufacturing cost for this connector 22. Further, the comb member 50 may be hit and damaged or broken by the end surface 58 of the connector 20 if this connector is too forcefully inserted into the connector 22. The resilient pressure pad member 156 applies a resilient force to the bend of the contacts 40, but is first of all required as a sealing member to prevent material of the molded body 30 from being squeezed into the cavity 36 during the molding of this body. This pad 156, and the necessity for its manufacture and placing in the connector 22 prior to molding of the body 30 adds significantly to the manufacturing costs for the connector 22.

SUMMARY OF THE INVENTION

In view of the deficiencies of conventional electrical cable connectors, it is a primary object for this invention to provide an electrical cable connector which avoids one or more of these deficiencies.

Another object for the present invention is to provide an improved durable electrical cable connector which is low in cost and very high in quality. That is, the electrical cable connector according to the present invention should provide long life and reliable, secure electrical connection between the conductors of connected cables.

Yet another object for the present invention is to provide an improved durable electrical cable connector which is polarized so that the conductors of connected cables are connected in only one order, with no possibility of incorrect connection of the conductors.

Accordingly, the present invention provides according to one aspect thereof a female electrical connector for connecting plural conductors of a multi-conductor electrical cable each individually to one of another corresponding plurality of electrical conductors, the electrical connector comprising: an insulative housing defining a blind cavity therein and an opening axially outwardly from the cavity, the housing defining axial alignment means extending from adjacent the opening axially along the cavity toward an end wall thereof, thereby to guide and receive into the cavity a matching male connector carrying such another plurality of corresponding electrical conductors; an axially extending printed circuit board carried by the insulative housing and including plural contact pads, electrical conductors of the cable each connecting individually with a corresponding one of the plural contact pads, plural solder pads spaced from the contact pads each individually surrounding a corresponding one of plural apertures defined by the printed circuit board; and plural conductive traces extending across the printed circuit board each individually connecting one of the plural contact pads to one of the plural solder pads; plural wire-like contact members received individually one into each aperture of the plural apertures and extending perpendicularly from the printed circuit board toward the cavity, the wire-like contact members being individually soldered to the corresponding one of the plural solder pads; the insulative housing defining a comb feature on the end wall thereof, the comb feature defining plural substantially parallel slots, each of the plural wire-like contact members including a free end portion which is movable received in a corresponding one of the slots of the comb feature between a first position extending diagonally across the cavity, and a second position in which the wire-like contact members are deflected by insertion of the male connector into the cavity of the female connector and into electrical engagement with a corresponding one of the other conductors.

These and other objects and advantages of the present invention will be apparent from a reading of the following detailed description of a single exemplary preferred embodiment of the present invention, taken in conjunction with the following drawing Figures, in which the same reference numeral refers to the same feature throughout the drawing Figures, or to features which are analogous in structure or function to one another.

DETAILED DESCRIPTION OF AN EXEMPLARY PREFERRED EMBODIMENT OF THE INVENTION

Figure 12:
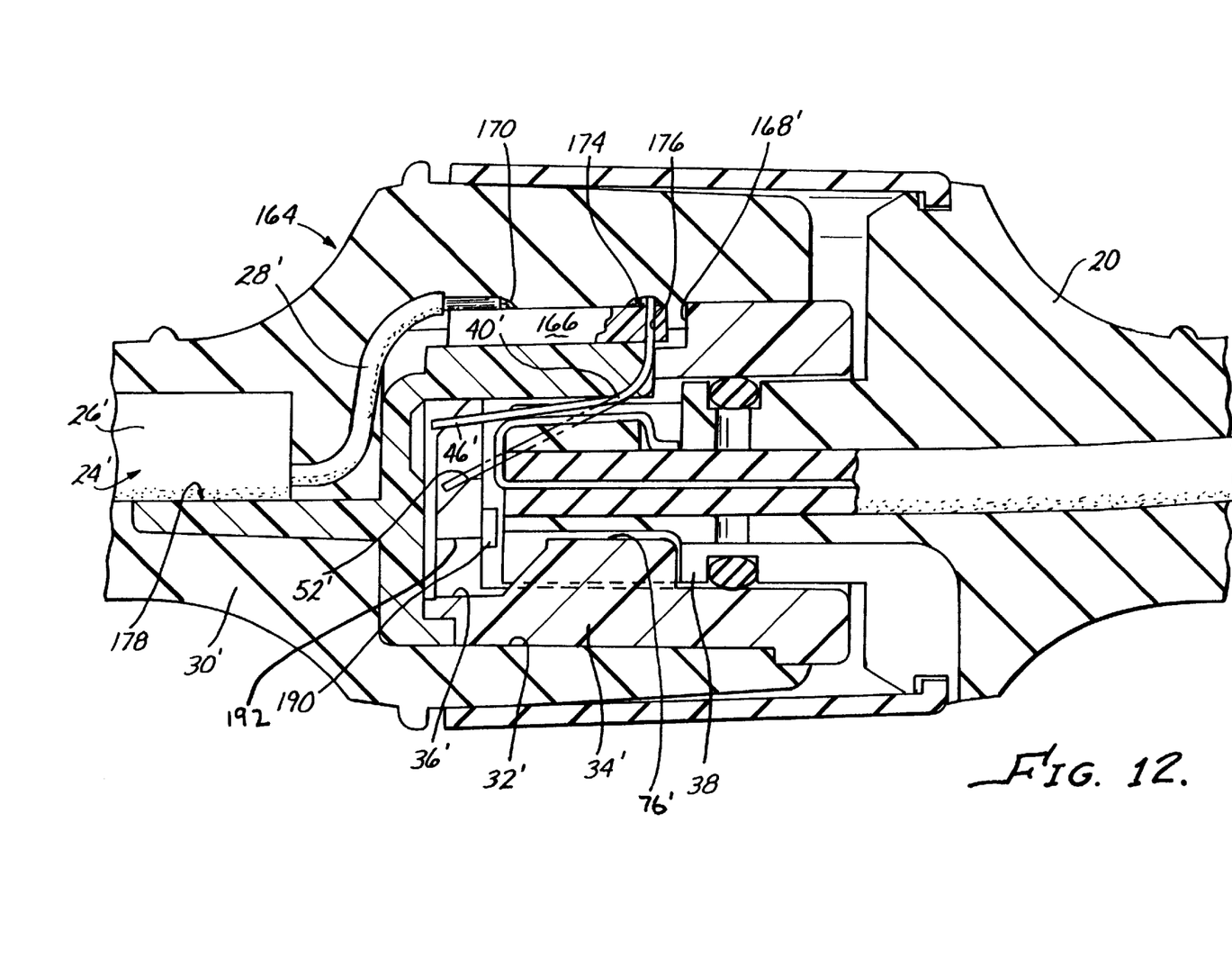
FIG. 12 is an enlarged fragmentary longitudinal cross sectional view similar to FIG. 3, but showing the disposable prior art male connector interconnected with an improved durable connector embodying the present invention.
Figure 13:
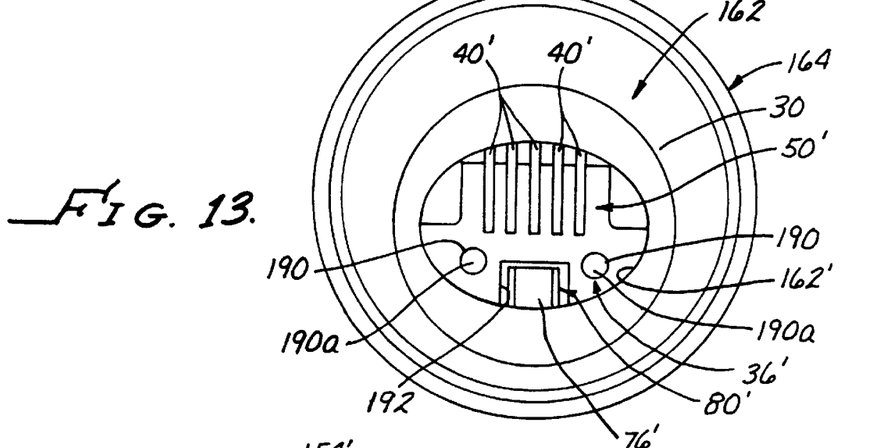
FIG. 13 is an enlarged end view of the durable improved cable connector embodying the present invention, and is similar to FIG. 2.
Figure 14:
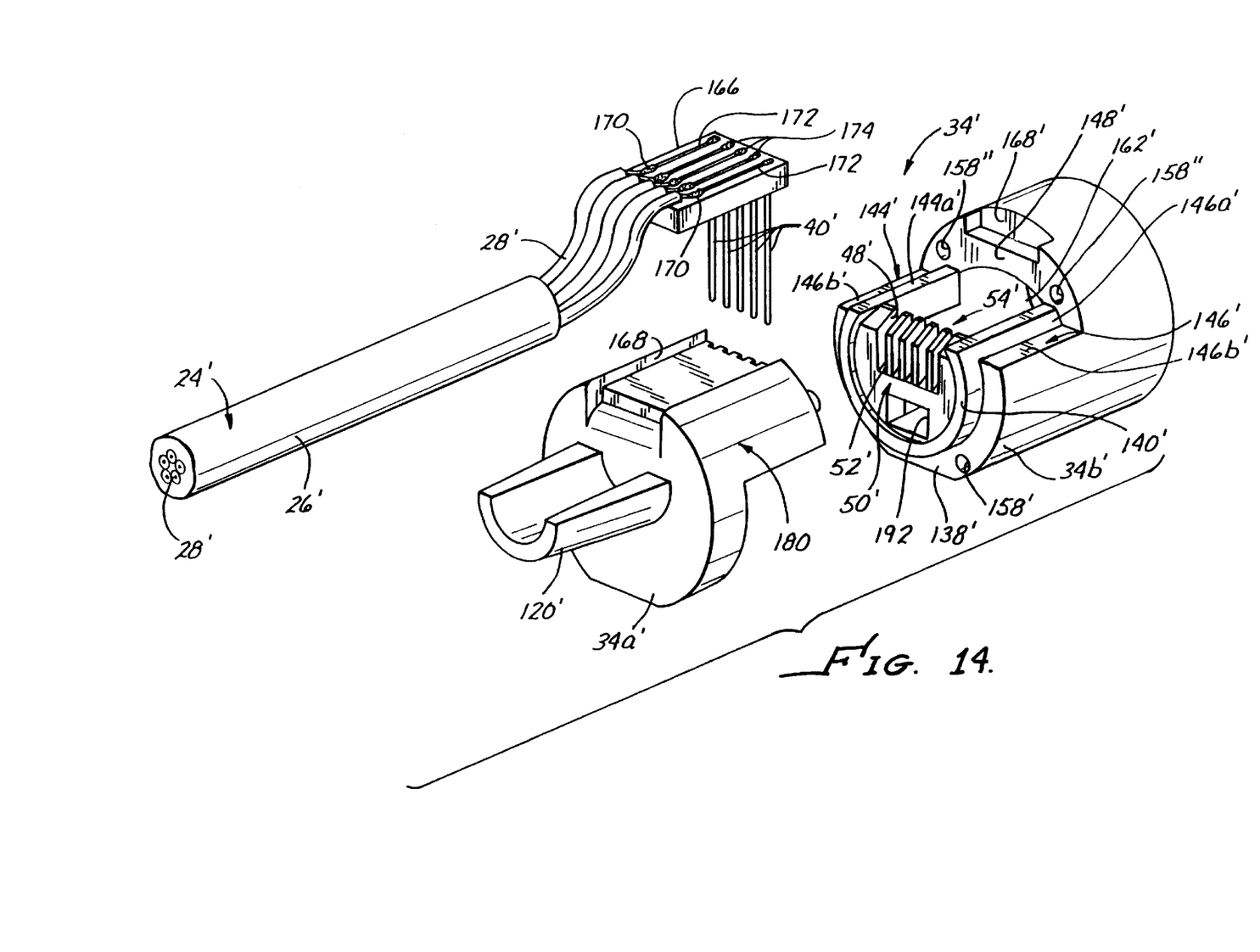
FIG. 14 provides a very greatly enlarged and exploded perspective view of parts of an improved durable connector embodying the present invention.

Viewing FIGS. 12–16, with particular attention first to FIGS. 12, 13, and 14, a improved durable connector 164 is shown first in fragmentary cross sectional view, in end view, and in partial exploded perspective view, similar to FIGS. 3, 2, and 9, respectively. The improved durable connector 164 is functionally equivalent to the conventional connector 22 shown in the drawing Figures discussed above, but is structurally improved, more reliable, more durable, and a full and functionally equivalent replacement for connector 22, with a user of the connectors 22 and 164 not being able to tell the two apart from external appearances except upon close inspection. In order to obtain reference numerals for use in describing the structural features and functional cooperations of such features, features which are the same or which are structurally or functionally equivalent to features depicted and described by reference to FIGS. 1–11 above are referenced with the same numeral in FIGS. 12–16, with a prime (') added thereto.

Connector 164 is carried on a length of cable 24'. Cable 24' includes an insulating jacket 26', and plural electrical conductors 28'. The connector 164 includes a body 30' of insulative material molded onto the cable 24', and defines a cavity 32' into which a preformed shape-retaining insulative member 34' is received. This pre-formed insulative member 34' defines a cavity 36' which is partially oval in end view, and into which the shape-matching and axially projecting portion 38 of the connector 20 is received. However, as FIGS. 13 and 14 show, the insulative housing 34' is outwardly of substantially circular cylindrical shape. Within the cavity 36', the connector 164 carries a laterally arrayed plurality of spaced apart resilient wire-like contacts 40'. These contacts 40' are each carried collectively by a printed circuit board member 166 which fits within a recess 168 defined on the upper side of the insulative member 34'.

As FIG. 14 shows, each respective one of the plural conductors 28' of the cable 24' is soldered to a corresponding one of a like plurality of contact pads 170 defined by the printed circuit board member 166. Each of these contact pads 170 is connected by a respective conductive trace 172 to a corresponding solder pad 174. The solder pads 174 each surround a respective one of a plurality of apertures 176. Contacts 40' are individually soldered onto the contact pads 174 and project through the apertures 176 toward cavity 36'. Also, the contacts 40' are each individually movable at a free end portion 46' thereof in a respective slot 48' defined by a comb portion 50' of the member 34'. As FIG. 12 shows in dashed lines, when the connectors 20 and 164 are not connected, the free end portions 46' normally rest upon a respective shelf feature 52' of the comb 50'. It will be understood that the free end portions 46' of the contacts 40' may at rest be disposed off of the shelf feature 52' and still function normally. When the connectors 20 and 164 are connected, the contacts 60 engage the contacts 40', and moves them to the solid line position seen in FIG. 12. The contacts 40' are positioned and movably spaced apart by the cooperation of the comb member 50' and the regular spacing of the plural apertures 176 defined by the printed circuit board member 166.

Figure 15:
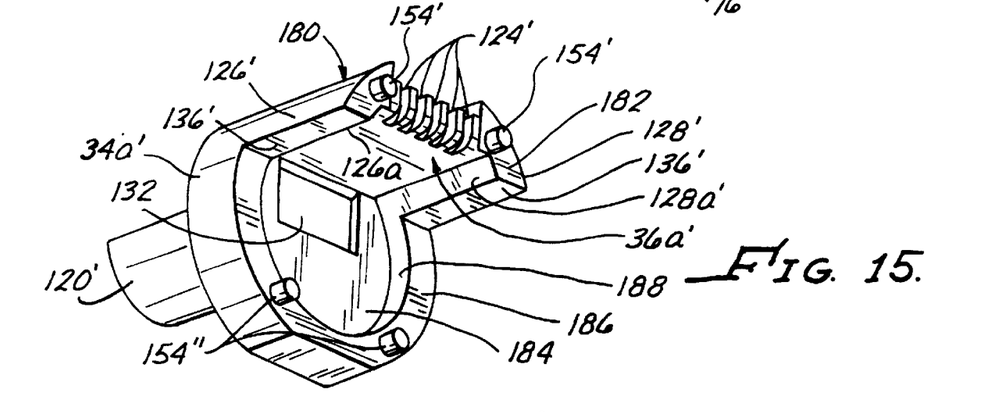
FIG. 15 is an enlarged perspective elevation view similar to FIG. 10, but showing a part of the improved durable connector embodying the present invention.

FIG. 14 in conjunction with FIGS. 12, 13, 15, and 16 depict the connector 164 in greater detail. FIG. 14 shows an exploded perspective view of the insulative member 34' of connector 164 at an intermediate stage of manufacture and prior to the molding of the body portion 30' around the cable 24' and insulative member 34'. As FIG. 14 shows more particularly, the insulative member 34' is formed of two cooperative parts, referenced with the numbers 34a' and 34b' on FIG. 14. It is seen in FIGS. 12, 14 and 15 that the recess 168, which is formed mostly in part 34a', with a portion 168' of this recess being formed in part 34b', includes plural arcuate grooves 124' extending from alignment with the apertures 176 to the cavity 36'. The contacts 40' extend along these grooves into the slots 48' of the comb 50'.

Viewing FIGS. 14 and 15, it is seen that the part 34a includes an arcuate tang 120' to which the cable 24' may be secured. The cable 24' may be secured to the tang 120' by use of a crimping sleeve 122, as was seen in FIG. 3. More preferably, the cable 24' is secured to the tang 120' by an anaerobic adhesive, indicated on FIG. 12 with the arrowed reference numeral 178. With the part 34a' and cable 24' so prepared with contacts 40', the projecting free end portions 46' of the contacts 40' extend perpendicularly to the printed circuit board member 166 as is illustrated in FIG. 14. The contacts 40' extend into the cavity 36 in parallel spaced apart relationship. As the parts 34a' and 34b' are united, the contacts 40' are bent rearwardly into the cavity 36' (the portion 36a' of which is formed in and bounded by the part 34a', as is best seen in FIG. 15). When the parts 34a' and 34b' are fully united, the contacts 40' have the positions indicated in FIG. 12.

Still viewing FIG. 15, it is seen that the part 34a' at an upper extent thereof includes a forwardly extending upper wall portion 180, which upwardly defines the recess 168. This wall portion 180 laterally includes a rather short (in the circumferential direction) pair of wall portions 126', 128' that extend toward the viewer of this Figure. Below and rearwardly of the upper wall portion 180, the part 34a' includes a lower wall portion 132'. The wall portions 126, 128, and 180 extend forwardly of the wall portion 132' to define a pair of opposite longitudinally extending side edge surfaces 136', one on each side of the part 34a'. The wall portions 126', 128' and 180 cooperatively define an axially disposed and transversely extending end surface 182. On this wall portion end surface 182 is disposed a pair of axially extending laterally spaced apart pegs 154'.

Below the wall portions 180, 126', and 128', and spaced behind these features, it is seen that the part 34a' defines at wall portion 132' an arcuate lower wall portion 184. The wall portion 184 carries a short arcuate axially-extending wall portion 186 extending axially toward the viewer of FIG. 15 to define a recess 188. Carried on the arcuate axially extending wall portion 186 is a pair of axially extending spaced apart and axially extending pegs 154". Consequently, the part 34a' in side elevation view (some what as seen in FIG. 14) defines a generalized Z-shaped surface configuration for interface with the part 34b', as will be seen.

Figure 16:
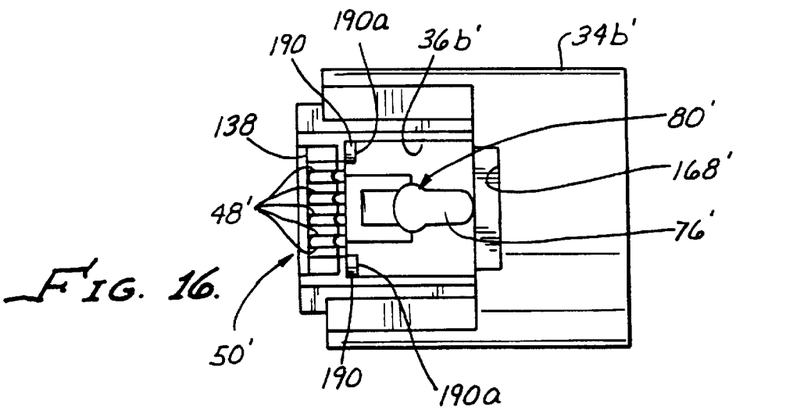
FIG. 16 is a plan view of another part of the improved durable connector embodying the present invention.

Viewing FIGS. 14 and 16, it is seen that the part 34b' also forms a generalized Z-shaped interface for cooperative engagement with the part 34a'. That is, part of this Z-shaped interface of the part 34b' is formed by a lower arcuate end wall portion 138' of the part 34b'. This arcuate end wall 138' carries an axially extending arcuate rib 140' which has the form of an axially extending arcuate tongue. The arcuate rib or tongue 140' is received into the recess 188 when the parts 34a' and 34b' are united. Outwardly of the arcuate rib 140', the part 34b' defines a pair of spaced apart blind holes 158' (only one of which is visible in the drawing Figures) for receiving the pegs 154'.

The part 34b' includes axially extending longitudinal side edge surfaces 144', 146', extending forwardly of the arcuate wall portion 138', and which each include a respective up-raised inner ridge portion 144a' and 146a', and respective ledge features (144b' and 146b', respectively) outwardly of these up-raised inner ridge portions 144a' and 146a'. The up-raised inner ridge portions 144a' and 146a' engage within depending lower inner surface portions 126a' and 128a' of walls 126' and 128' (seen in FIG. 15), while the ledge portions 144b' and 146b' engage the lower edge surfaces of these wall portions 126' and 128' of the part 34a'.

In order to cooperate with the wall portions 126, 128, and 180 of the part 34a', the part 34b' also includes a comparatively small radially extending and axially disposed wall portion generally referred to with the numeral 148'. This wall portion 148' defines a pair of rearwardly opening blind holes 158" which receive the pair of pegs 154' when the parts 34a' and 34b' are united as depicted in FIG. 12.

Viewing FIGS. 13 and 14, it is seen that the part 34b' defines an oval opening 162' to the cavity portion 36b' defined within the part 34b', and to the cavity 36' in general defined within the parts 34a' and 34b' when these parts are united. It will be understood that because the connector 164 is functionally equivalent to the conventional connector 22 described above, the shape and size of cavity 36' substantially matches that of cavity 36. FIGS. 14 and 16 viewed in concert with one another show that the arcuate end wall portion 138' of the part 34b' defines plural parallel slots 48' which are spaced apart to define a comb portion of this wall, generally referenced with the numeral 50'.

However, in contrast to the conventional connector 22 described in detail above, the comb portion 50' of the connector 164 is not merely supported by a portion 76a of a key member 76. The comb portion 50' is a part of the wall 138', and is supported substantially entirely around its circumference except for the cord of this circular feature occupied by the openings (referenced with arrowed numeral 54a on FIG. 14) for slots 54'. Consequently, this comb feature 50' is much stronger than the comb feature of the conventional connector 22, and will not be broken even by an overly forceful insertion of the connector part 20 into the connector 164.

In order to further protect the comb feature 50' from being damaged by such overly forceful insertion of the connector 20, the side of wall 138' facing the cavity 36' defines a pair of spaced apart circular stops 190 (best seen in FIGS. 12, 13, and 16). These stops 190 each have an axially disposed end surface 190a, which is contacted by the end surface 58 of the connector 20 upon this connector being inserted into cavity 36' of the connector 164 (as is seen in FIG. 12). Because the stops 190 are disposed closely to the supported sides of wall portion 138', these stops 190 are strong and well prevent the connector 20 from being inserted too far into cavity 36'. Consequently, the end surface 58 of connector 20 can never come into forceful contact with the comb portion 50' of the connector 164. The comb portion 50' of the connector 164 is thus not subject to accidental breakage in this way, which breakage did occasionally happen with the conventional connector 22.

Further viewing FIGS. 14 and 16, it is seen that the key 76' carried upon the part 34b' includes an integral lateral enlargement, referenced with the numeral 80' because it serves the same purpose as the pin 80 of the conventional connector 22. The wall portion 138' of the part 34b' defines a rectangular window 192 which aligns axially with the key 76'. In the manufacturing of the connector 164, the parts 34a' and 34b' are injection molded. When part 34b' is molded, an axially extending die part or core of the axially moving die half extends through the window 192 to cooperate with a core portion of the fixed die half in forming the protrusion 80' on the key 76'. As a result, the connector part 34b' may be injection molded using dies which open in the axial direction only, without the need for any radially moving die cores or pins (i.e., such as those necessary for the formation of the hole for pin 80 in the conventional connector 22). This simplification in the injection molding operation for the part 34b' reduces the costs for the connector 164 significantly. Also, as was mentioned above, the insulative member 34' of the connector 164 outwardly is circular in sectional shape. This shape for the parts 34a' and 34b' of the insulative member 34' makes the fabrication of injection molding dies for these parts considerably easier and less expensive than the complex shape required for the insulative member 34 of conventional connector 22.

When the connector parts 34a' and 34b' have been prepared as described above, and are united with one another preparatory to the molding of the body 30' around the housing 34', the Z-shaped interface between these parts is joined and sealed by use of an anaerobic adhesive. Such adhesive seals the interface of the parts 34a' and 34b' so that no resilient sealing member (such as member 156 of the conventional connector 22) is required to prevent the plastic material of the body 30' from squeezing into the cavity 36 during the injection molding operation. This freedom from the requirement to fabricate and install such a sealing member further reduces the costs for the improved connector 164.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

We claim:

1. A female electrical connector molded onto a distal end of a cable and adapted to mate with a male connector, comprising:

a length of cable having a plurality of conductor wires enclosed within a sheath-like insulative jacket;

an insulative female connector assembly having a distally opening blind cavity for receiving a male connector inserted therein, the cavity defining an axis extending in a proximal-distal orientation;

an axially extending outer wall portion on the assembly defining an outer recess and a plurality of openings in the recess arrayed transversely to the axis;

a comb on the assembly located within the cavity and proximally with respect to the openings, the comb defining a plurality of alternating teeth and slots arrayed transversely to the axis;

a printed circuit board positioned in the recess of the outer wall portion and having a plurality of contact pads on a proximal end to which the cable conductor wires are soldered;

a plurality of apertures extending through the circuit board in registration with the openings;

a plurality of resilient wire-like contacts soldered into the circuit board apertures and projecting through the openings into the cavity, a free end of each contact being bent proximally and captured in an associated slot of the comb while remaining free to be displaced proximally;

a plurality of conductive traces on the circuit board connecting respective pairs of contact pads and contacts; and an insulative outer body molded over the cable sheath, conductors, circuit board, and connector assembly, and leaving the cavity open in the distal direction.

2. The connector of claim 1, wherein the connector assembly comprises separate proximal and distal halves joined together, and wherein the outer wall portion is formed on the proximal half.

3. The connector of claim 2, wherein the wall portion includes arcuate grooves formed on a distal end thereof, and the distal half includes a proximally facing wall against which the distal end of the wall portion abuts, wherein the openings are formed between the grooves and the proximally facing wall.

4. The connector of claim 2, wherein the proximal half includes an end wall defining a proximal end of the blind cavity, the end wall having a tang extending proximally therefrom outside of the cavity with an arcuate groove for receiving the cable insulative jacket, wherein the jacket terminates at the end wall and the conductor wires continue therefrom around the end wall to connect with the contact pads on the circuit board on the outside of the outer wall portion.

5. The connector of claim 1, wherein the assembly comprises an outer wall surrounding the cavity and partially formed by the outer wall portion, the assembly further including a comb wall positioned within the cavity proximally with respect to the openings and transversely to the axis, the comb being formed on the comb wall with the teeth projecting toward the outer wall portion and terminating in free ends spaced from the outer wall portion and together defining an edge of the comb wall, the comb wall being rigidly connected to the outer wall on all sides except for the edge.

6. The connector of claim 5, wherein the distal half is injection molded and the comb wall forms a part thereof, the distal half further including a key for mating with a male connector, the key projecting into the blind cavity from an inner surface of the outer wall and distally with respect to the comb wall, wherein the comb wall further includes a window through which a mold tool axially inserts to form a proximal side of the key.

7. A female electrical connector molded onto a distal end of a cable and adapted to male with a male connector, comprising:

a length of cable having a plurality of conductor wires enclosed within a sheath-like insulative jacket;

an insulative female connector assembly having a proximal half coupled to an injection molded distal half, the assembly having a distally opening blind cavity for receiving a male connector inserted therein, the cavity defining an axis extending in a proximal-distal orientation;

an axially extending outer wall portion defining a plurality of openings arrayed transversely to the axis;

a key formed on the distal half for mating with a male connector, the key projecting into the blind cavity from an inner surface of the outer wall;

a comb wall formed on the distal half including a comb defined by a plurality of teeth with slots therebetween, the comb wall being positioned within the cavity proximally with respect to the openings, proximally with respect to the key and transversely to the axis, wherein the comb wall further includes a window to enable a mold tool to axially insert and form a proximal side of the key; and a plurality of resilient wire like contacts electrically connected to the conductor wires and projecting from outside the cavity through the openings into the cavity, a free end of each contact being bent proximally by the comb upon joining the proximal and distal halves and being captured in an associated slot of the comb while remaining free to be displaced proximally.

8. The connector of claim 7, wherein the outer wall portion defines an outer recess, the connector further comprising a printed circuit board positioned in the recess and having a plurality of contact pads on a proximal end to which the cable conductor wires are soldered, the circuit board further including a plurality of conductive traces connecting respective pairs of contact pads and contacts, the connector further including an insulative outer body molded over the cable sheath, conductors, circuit board, and connector assembly while leaving the cavity open distally.

9. The connector of claim 7, wherein the assembly comprises an outer wall surrounding the cavity and partially formed by the outer wall portion, the outer wall portion being formed on the proximal half and the remaining outer wall being formed by the distal half, the cavity terminating at a proximal end by an end wall of the proximal half, wherein the comb wall is positioned close to a distal face of the end wall.

10. The connector of claim 9, wherein the outer wall is generally cylindrical in transverse cross-section, and the cavity is generally oval in transverse cross-section.

11. The connector of claim 7, wherein the comb teeth project toward the outer wall portion and terminate in free ends spaced from the outer wall portion and together defining an edge of the comb wall, the comb wall being connected to the outer wall on all sides except for the edge.

12. A method of assembling a female electrical connector adapted to mate with a male connector, comprising:

stripping an insulative jacket from a free end of a cable to form an end of the jacket and expose a plurality of conductors extending therefrom;

attaching the jacket end to a proximal end of a proximal half of a molded connector assembly;

providing a printed circuit board having a plurality of conductive traces thereon, each of the conducive traces terminating at one end of the circuit board in a contact pad and at the other end of the circuit board in an aperture;

soldering a plurality of resilient, wire-like contacts within the apertures to extend generally perpendicularly to the plane of the circuit board;

positioning the circuit board in a recess formed on the proximal half so that the contacts extend over a distal edge of the proximal half;

electrically connecting the conductors to the contact pads;

axially displacing the proximal half toward a distal half of the connector assembly so that a comb formed on the distal half receives the contacts in slots and bends the contacts proximally, the proximal and distal halves defining therein a blind cavity within which the contacts are exposed; and molding an outer body around the cable jacket, conductors, circuit board, and connector assembly while leaving the cavity open distally.

13. The method of claim 12, further including injection molding the distal half of the connector assembly, including the steps of:

forming an outer wall of the cavity;

forming a comb wall within the cavity on which is formed the comb;

forming a window in the comb wall;

forming a key on an inner surface of the outer wall distally with respect to the comb wall, the key having a lateral enlargement partially formed by a moveable mold die; and axially retracting the mold die from within the cavity through the window.

14. The method of claim 12, further including injection molding the distal half of the connector assembly, including the steps of:

forming an outer wall of the cavity;

forming a comb wall within the cavity on which is formed the comb; and connecting the comb wall to the outer wall on all edges except the comb edge.

* * * * *